United States Patent [19]

Waldron

[11] Patent Number: 5,222,956
[45] Date of Patent: Jun. 29, 1993

[54] SURGICAL DRILL COLLET MECHANISM AND BUR

[75] Inventor: Stephen H. Waldron, Camarillo, Calif.

[73] Assignee: Altair Instruments, Inc., Ventura, Calif.

[21] Appl. No.: 908,358

[22] Filed: Jul. 6, 1992

[51] Int. Cl.⁵ .............................................. A61B 17/56
[52] U.S. Cl. ................................................... 606/80
[58] Field of Search ................. 606/79, 80; 279/1 B, 279/1 F; 423/128, 129, 102, 116, 127, 225, 81; 81/177.85

[56] References Cited

U.S. PATENT DOCUMENTS

| | | | |
|---|---|---|---|
| 1,636,421 | 7/1927 | Knott | 433/128 |
| 4,007,528 | 2/1977 | Shea | 433/128 |
| 4,014,099 | 3/1977 | Bailey | 433/128 |
| 4,055,185 | 10/1977 | Waldron | 433/128 |
| 4,378,212 | 3/1983 | Waldron | 433/128 |
| 4,661,062 | 4/1987 | Seigneurin | 433/128 |
| 4,728,292 | 3/1988 | Lustig | 433/128 |
| 4,940,410 | 7/1990 | Apap | 433/128 |
| 5,028,181 | 7/1991 | Jenkins | 433/128 |
| 5,037,299 | 8/1991 | Nakanishi | 433/129 |

*Primary Examiner*—Michael A. Brown
*Attorney, Agent, or Firm*—Marvin E. Jacobs

[57] ABSTRACT

A surgical drill uses burs with circular grooves about the circumference that are polygon shaped in cross section but curved along the length of the bur so as to accept locking balls therein. The burs slide within a tubular drive shaft that has transverse holes therein to guide the locking balls. A cylindrical cam surrounds the drive shaft and the locking balls to urge the balls radially inward into the bur groove. The cam is spring loaded axially. A spring loaded central pin within the drive shaft slides between the balls and urges the balls radially outward when no bur is inserted. A thumb button is used to disengage the ball surrounding cam.

8 Claims, 1 Drawing Sheet

SURGICAL DRILL COLLET MECHANISM AND BUR

TECHNICAL FIELD

This invention pertains to surgical drills, especially drills for otological neurosurgery. More specifically, a collet design is disclosed that accepts and positively locks in place a special bur shaft design.

BACKGROUND OF THE INVENTION

Prior art drill collet mechanisms typically grasp removable burs with frictional, magnetic, or latch engagement schemes. The inventor of the instant application is the inventor of U.S. Pat. No. 4,378,212 which describes a magnetic system for holding detachable burs and also describes, in some detail, about a dozen other pertinent prior art patents. U.S. Pat. No. 4,378,212, its teachings, and the prior art referred to therein, are hereby incorporated by reference into this application.

Surgeons, particularly neurosurgeons, prefer a drill with as small a diameter as possible in order to ease access to very small and delicate areas. However, the apparatus needed inside the drill to permit a variety of drill burs to be easily and quickly inserted and removed from the drill necessitates larger diameter drills. The prior art designs referred to above are less than satisfactory in this respect. The present invention provides an unusually compact arrangement wherein burs are solidly locked in place, for rotation of the drill in either direction, while still allowing quick and easy removal and maintaining a very narrow diameter drill.

SUMMARY OF THE INVENTION

Briefly, a unique bur is disclosed which has a circumferential indentation about the shaft to receive small surrounding locking balls therein to lock the bur within the drill. The bottom of the indentation comprises several straight sections as they progress around the circumference of the bur shaft, so as to rotationally lock the bur into the rotating drill driver and balls. However, the indentation bottoms are curved as they progress in the direction along the axis of the bur, at a radius matching the locking balls, so as to eliminate any axial movement of the bur. A cylindrical cam surrounds the locking balls to hold the balls in the indentation, the cam urged toward the locked position by a spring. To remove the bur, a small button on the side of the drill is pushed toward the bur end of the drill, which in turn slides a cylindrical cam mover inside the drill. The cam mover pushes the cylindrical cam into the unlocked position so that the locking balls can move radially out of the indentation in the bur shaft. The locking balls are urged outward by a spring loaded pin that rests within, and at the bottom of, the central tube that the bur occupies. The use of cylindrical cams, springs, locking balls, and cam movers results in a very small diameter surgical drill as will become apparent upon consideration of the following more detailed description and drawings.

DETAILED DESCRIPTION OF THE INVENTION

Figure 1:
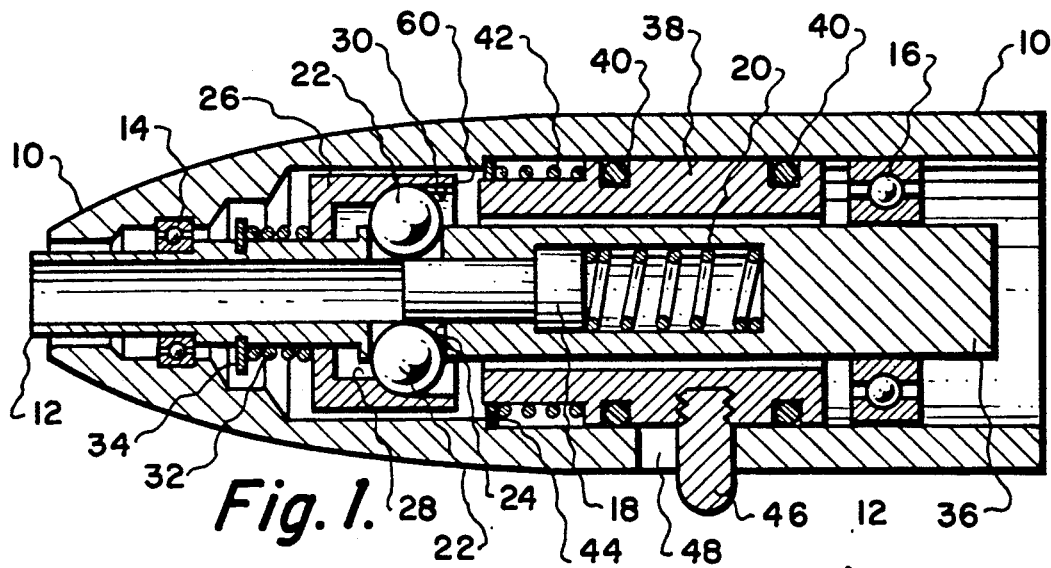
FIG. 1 is a sectional view of the drill of the present invention, with no bur inserted, in order to show the rest position of the locking balls, cylindrical cam, central pin, and cam mover.

FIG. 1 has been greatly expanded in scale to enhance clarity. It should be understood that the actual drill is about eight times narrower, that is, in the vertical direction in FIG. 1, and about four times shorter in the horizontal direction.

A cylindrical or tubular drill housing 10 is sectionally shown in FIG. 1. A tubular drive shaft 12 extends the length of housing 10, supported inside housing 10 by a forward bearing 14 and a rearward bearing 16 in a manner well known to those skilled in the art. A central T-shaped pin 18 is urged forward inside shaft 12 by a spring 20 so as to spread a pair of locking balls 22 radially outward through holes 24 in shaft 12. Locking balls 22 are restrained from further outward movement by a cylindrical cam 26 that surrounds balls 22. The inside surface of cam 26 has a lesser radius surface 28 at the forward end and a larger radius surface 30 at the rearward end. Cam 26 is urged rearward by a spring 32 acting against a retaining ring 34 mounted about shaft 12. Drive shaft 12 is turned by a conventional means well known to those skilled in the art, connected to shaft 12 at its rearward end 36.

Surrounding shaft 12 is a cylindrical cam mover 38 that slides along the interior surface of housing 10, spaced slightly from housing 10 by a pair of O-rings 40. O-rings 40 keep dust out of the high speed rotating parts of the drill. Cam mover 38 is urged rearward by a spring 42 acting against a retaining and sealing washer 44. A button 46 is threaded into cam mover 38 and extends out of housing 10 through a slot 48.

Figure 2:
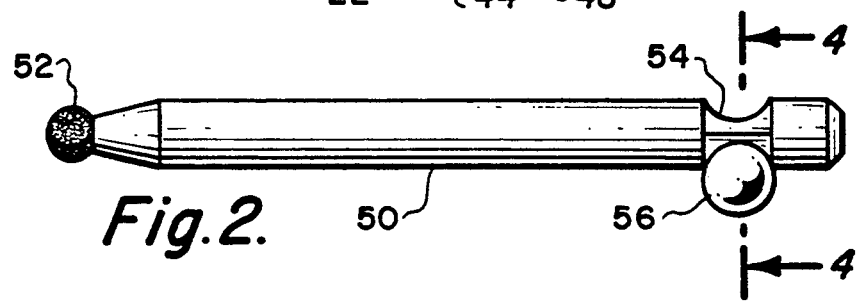
FIG. 2 shows a typical bur with an indentation having circumferentially straight but axially curved surfaces to accept the locking balls.
Figure 3:
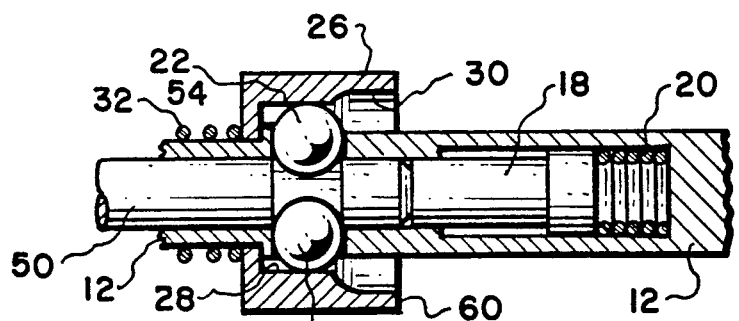
FIG. 3 is a fragmentary sectional view of the central portion of the FIG. 1 section, but showing the new position of the balls, cam, and pin when the bur is inserted into the drill.
Figure 4:
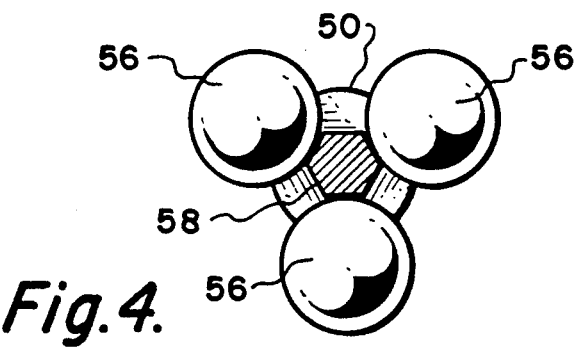
FIG. 4 is a sectional view, taken on line 4—4 in FIG. 2, that shows how the locking balls enter the indentation for an embodiment that uses three balls and six straight segments at the bottom of the indentation.

The special bur design of the present invention is shown in FIG. 2. A circular shaft 50 is sized to fit snugly within the forward end of shaft 12. A variety of cutting heads 52 may be provided at the forward end of bur shaft 50. A circumferential indentation 54 encircles bur shaft 50. Indentation 54 is curved to match the curve of the locking ball 56 with regard to the profile along the axial length of the bur shaft 50. However, the profile of the bottom of the indentation viewed orthogonally to bur shaft 50 is that of a series of straight segments, as can be seen in the cross sectional view of FIG. 4. If a six sided indentation 54 is used, as in FIG. 4, a hexagon shaped indentation bottom 58 results which can engage three or six locking balls. Three balls 56 are shown in FIG. 4. FIG. 3, by contrast, shows a four sided indentation so that two locking balls 22 can be easily seen in the drawing plane. Many combinations of straight indentation bottom segments and balls are obviously within the scope of the invention. Three straight segments may be used with three balls. Four balls may be used on four segments. However, the FIG. 4 arrangement has been found to be very efficient.

If bur 50 is inserted into drive shaft, as shown in the fragmentary section of FIG. 3, central pin 18 is forced rearward, compressing spring 20 as shown. When indentation 54 reaches locking balls 22, balls 22 fall radially inward into indentation 54, urged there by the action of cylindrical cam 26 and spring 32. The bur shaft is, thus, firmly and quickly locked in place so as turn with drive shaft 12. To replace the bur, the user simply slides button 46 forward along slot 48, thus sliding cam mover 38 against the end 30 of cam 26 so as to move cam 26 forward, once again compressing spring 32. The bur 50 can then be extracted, expanding balls 22 out to the greater radius surface 30. Central pin 18, under the action of spring 20, follows the bur forward so as to once again hold the locking balls 22 outward as in the FIG. 1 position.

The cylindrical cam and ball locking structure permits a very slim drill that fits into quite small spaces while still affording a positive retention of the bur and quick and easy removal of the bur.

Since variations in the indentation shape, number of locking balls, spring configurations, cam shape, and cam mover are possible without departing from the spirit and scope of the invention, limitation in accordance only with the appended claims is appropriate.

I claim:

1. A surgical drill adapted to receive a cooperating bur comprising in combination:
   a tubular housing;
   a tubular drive shaft mounted for rotation within said housing, said drive shaft having a plurality of radial holes therethrough;
   a plurality of locking balls disposed within said holes;
   a spring urged central pin within said drive shaft adapted to move between said balls and thereby press said balls radially outward through said holes;
   a spring urged cylindrical cam encircling said drive shaft, said cam adapted to move to surround said balls and thereby press said balls radially inward through said holes;
   a drilling bur adapted to fit within said tubular drive shaft, said bur having an indentation positioned to receive said balls therein so as to axially and rotationally lock the bur to the drive shaft; and
   cam moving means in said housing adapted to be moved against said cam so as to move said cam away from the ball surrounding position so as to allow extraction of the bur.

2. The apparatus of claim 1 in which the bottom surface of said indentation in said bur is curved along the axial length of said bur so as to generally match the curvature of said locking balls but in which said same bottom surface comprises a series of straight segments along the circumferential length of said bur.

3. The apparatus of claim 2 in which there are four straight segments and two locking balls.

4. The apparatus of claim 2 in which there are six straight segments and three locking balls.

5. The apparatus of claim 1 in which said cam moving means comprises a cylindrical member surrounding said drive shaft, but not contacting said drive shaft, and slidable on the interior surface of said housing, said cylindrical member having a button extending out through a slot in said housing to facilitate moving said moving means.

6. The apparatus of claim 5 in which the bottom surface of said indentation in said bur is curved along the axial length of said bur so as to generally match the curvature of said locking balls but in which said same bottom surface comprises a series of straight segments along the circumferential length of said bur.

7. The apparatus of claim 6 in which there are four straight segments and two locking balls.

8. The apparatus of claim 6 in which there are six straight segments and three locking balls.

* * * * *